US011413683B2

(12) United States Patent
Jaramillo Botero et al.

(10) Patent No.: US 11,413,683 B2
(45) Date of Patent: Aug. 16, 2022

(54) SYNTHESIS OF FUNCTIONALISED GOLD NANOPARTICLES AND NANOCOMPOUNDS CONTAINING SAME FOR MEASURING SUCROSE OR STARCH IN CELLS (71) Applicants: PONTIFICIA UNIVERSIDAD JAVERIANA, Cali (CO); CENTRO INTERNACIONAL DE AGRICULTURA TROPICAL—CIAT, Cali (CO)

(72) Inventors: Andres Jaramillo Botero, Cali (CO); Diana Patricia Hermith Ramirez, Cali (CO); Pedro Hernandez, Cali (CO)

(73) Assignees: PONTIFICIA UNIVERSIDAD JAVERIANA, Cali (CO); CENTRO INTERNACIONAL DE AGRICULTURA TROPICAL—CIAT, Cali (CO)

( * ) Notice: Subject to any disclaimer, the term of this patent is extended or adjusted under 35 U.S.C. 154(b) by 554 days.

(21) Appl. No.: 16/474,020

(22) PCT Filed: Dec. 28, 2017

(86) PCT No.: PCT/IB2017/058461
§ 371 (c)(1),
(2) Date: Jun. 26, 2019

(87) PCT Pub. No.: WO2018/122763
PCT Pub. Date: Jul. 5, 2018

(65) Prior Publication Data
US 2019/0381565 A1   Dec. 19, 2019

(30) Foreign Application Priority Data
Dec. 30, 2016   (CO) ......................... NC2016/0006180

(51) Int. Cl.
G01N 33/58 (2006.01)
B22F 1/14 (2022.01)
B22F 1/054 (2022.01)
B82Y 30/00 (2011.01)
B82Y 40/00 (2011.01)
C08G 75/26 (2006.01)

(52) U.S. Cl.
CPC ............... B22F 1/14 (2022.01); B22F 1/054 (2022.01); G01N 33/582 (2013.01); G01N 33/587 (2013.01); B22F 2301/255 (2013.01); B82Y 30/00 (2013.01); B82Y 40/00 (2013.01); C08G 75/26 (2013.01); C08K 2201/011 (2013.01); G01N 2400/16 (2013.01)

(58) Field of Classification Search
CPC ............ G01N 21/6428; G01N 33/582; G01N 33/5308; G01N 33/587; G01N 2400/16; G01N 2021/6441; C07F 1/12; B22F 9/24; B22F 1/102; B22F 1/054; B22F 1/14; B22F 2301/255; C08G 75/26; B82Y 40/00; B82Y 30/00; C08K 2201/011
See application file for complete search history.

(56) References Cited

U.S. PATENT DOCUMENTS

| 2009/0020048 A1 | 1/2009 | Hunsinger |
| 2013/0065777 A1 | 3/2013 | Altug et al. |
| 2017/0219548 A1 | 8/2017 | Troyer et al. |

FOREIGN PATENT DOCUMENTS

| DE | 102014203254 A1 | 8/2015 |
| KR | 20110122320 A | 11/2011 |
| WO | 2016/18798 A1 | 2/2016 |

OTHER PUBLICATIONS

Chhour et al. Labeling monocytes with gold nanoparticles to track their recruitment in atherosclerosis with computed tomography. Biomaterials 2016, vol. 87, pp. 93-103. (Year: 2016).*
Zhang et al. Functional gold nanoparticles for sensing applications. Nanotechnol Rev. 2013, vol. 2, No. 3, pp. 269-288. (Year: 2013).*
Xia et al., "Glucose oxidase-functionalized fluorescent gold nanoclusters as probes for glucose", Analytica Chimica Acta 772: 81-86 (2013).
Bagheri et al., "Noninvasive glucose measurement by fluorescence quenching of non toxic gold nanoparticles", Optics & Laser Technology 58: 135-138 (2014).
Keshvari et al., "A selective, sensitive and label-free visual assay of fructose using anti-aggregation of gold nanoparticles as a colorimetric probe", Chinese Chemical Letters 27: 847-851 (2016).
Chen et al., "A dual-mode signaling response of a AuNP-fluorescein based probe for specific detection of thiourea", Analyst, 141: 2581-2587 (2016).
Turkevich et al., "A Study of the Nucleation and Growth Processes in the Synthesis of Colloidal Gold", View Article Online, Journal Homepage: 55-75 (1951).
Jain et al., "Au nanoparticles target cancer", nanotoday, 2(1): 18-29 (2007).
Kuhnke et al., "C60 Exciton Quenching near Metal Surfaces", Physical Review Letters, 79(17): 3246-3249 (1997).
Martin et al., "Charged Gold Nanoparticles in Non-Polar Solvents: 10-min Synthesis and 2D Self-Assembly", Langmuir 26(10): 7410-7417 (2010).
Persson et al., "Electron-hole-pair quenching of excited states near a metal", Physical Review B 26(10): 5409-5415 (1982).

(Continued)

Primary Examiner — Shafiqul Haq
(74) Attorney, Agent, or Firm — Merchant & Gould P.C.

(57) ABSTRACT

The present invention relates to the field of industrial processes for measuring sugars and starch in cells and concerns the process of functionalising synthesized gold nanoparticles functionalized with polymer ligands, for the selective measurement of sucrose or starch in intracellular fluid. Also disclosed is a nanocompound for measuring the concentration of sucrose or starch in intracellular fluid, which contains synthesized gold nanoparticles functionalized with polymer ligands.

4 Claims, 6 Drawing Sheets (56) References Cited

OTHER PUBLICATIONS

Chance et al., "Fluorescence and energy transfer near interfaces: The complete and quantitative description of the Eu+3/mirror systems", The Journal of Chemical Physics, 63(4): 1589-1595 (1975).

Dulkeith, et al., "Fluorescence Quenching of Dye Molecules near Gold Nanoparticles:Radiative and Nonradiative Effects", Physical Review Letters, 89(20): 203002-1-203002-4 (2002).

Jares-Erijman et al., "FRET imaging", Nature Biotechnology 21(11): 1387-1395 (2003).

Ghosh et al., "Gold and silver nanoparticles based superquenching of fluorescence: A review", Journal of Luminescence 160: 223-232 (2015).

Ray et al., "Gold Nanoparticle Based FRET for DNA Detection", Plasmonics 2: 173-183 (2007).

Wang et al., "Identification of a UDP-glucose pyrophosphorylase from cotton (*Gossypium hirsutum* L.) involved in cellulose biosynthesis in *Arabidopsis thaliana*", Plant Cell Rep 30: 1303-1312 (2011).

Bagal-Kestwal et al., "Invertase-nanogold clusters decorated plant membranes for fluorescence-based sucrose sensor", Journal of Nanobiotechnology 13:30 (2015).

Medintz et al., "Materials for Fluorescence Resonance Energy Transfer Analysis: Beyond Traditional Donor-Acceptor Combinations", Reviews, Bioanalysis, Angewandte Chemie Int. Ed, 45:4562-4588 (2006).

Yun et al., "Nanometal Surface Energy Transfer in Optical Rulers, Breaking the FRET Barrier", J. Am. Chem. Soc. 127: 3115-3119 (2005).

Koo Lee et al., "Nanoparticle PEBBLE Sensors in Live Cells and In Vivo", Annual Rev. Anal.Chem 2: 57-76 (2009).

Alivisatos et al., "Nonclassical behavior of energy transfer from molecules to metal surfaces: Biacetyl/($3n\pi^*$)/Ag (111)", The Journal of Chemical Physics, 82(1): 541-547 (1985).

Aslan et al., "Saccharide Sensing Using Gold and Silver Nanoparticles—A Review", Journal of Fluorescence 14(4): 391-400 (2004).

Tiessen et al., "Subcellular compartmentation of sugar signaling: links among carbon cellular status, route of sucrolysis, sink-source allocation, and metabolic partitioning", Frontiers in Plant Science, Mini Review Articule, 3, Article 306: 1-6 (2013).

Elfeky et al., "Synthesis and Spectral Characteristics of Gold Nanoparticles Labelled with Fluorescein Sodium", Current Nanoscience 7: 1028-1033 (2011).

Perrault et al., "Synthesis and Surface Modification of Highly Monodispersed, Spherical Gold Nanoparticles of 50-200 nm", J. Am. Chem. Soc. 131: 17042-17043 (2009).

Brust et al., "Synthesis of Thiol-derivatised Gold Nanoparticles in a Two-phase Liquid-Liquid System", J. Chem., Chem.Commun: 801-802 (1994).

Tang et al., "A New Nanobiosensor for Glucose with High Sensitivity and Selectivity in Serum Based on Fluorescence Resonance Energy Transfer (FRET) between CdTe Quantum Dots and Au Nanoparticles", Full Paper, Chem. Eur. J., 14: 3637-3644 (2008).

Srivastava et al., "Biogenic synthesis and characterization of gold nanoparticles by *Escherichia coli* K12 and its heterogeneous catalysis in degradation of 4-nitrophenol", Nanoscale Research Letters, 8:70: 1-9 (2013).

Sharma et al., "Biogenic synthesis of nanoparticles: A review", Arabian Journal of Chemistry: 1-25 (2015).

Thakkar et al., "Biological synthesis of metallic nanoparticles", Nanomedicine: Nanotechnology, Biology, and Medicine: 1-6 (2009).

International Search Report for PCT/IB2017/058461, dated Apr. 3, 2018.

\* cited by examiner

SYNTHESIS OF FUNCTIONALISED GOLD NANOPARTICLES AND NANOCOMPOUNDS CONTAINING SAME FOR MEASURING SUCROSE OR STARCH IN CELLS

This application is a National Stage Application of PCT/IB2017/058461, filed Dec. 28, 2017, which claims the benefit of priority to Patent Application No. NC2016/0006180, filed Dec. 30, 2016 in Columbia, which applications are incorporated herein by reference. To the extent appropriate, a claim of priority is made to each of the above disclosed applications.

FIELD OF THE INVENTION

The present invention is related to the field of processes of measurement of sugars and starch in cells.

BACKGROUND OF THE INVENTION

The research related to biosensors has experienced an explosive growth in the last decades. A biosensor is generally defined as an analytical device that converts a biological response into a processable and quantifiable serial (Lowe, C. R. Biosensors, Trends in Biotechnology 1984, 2 (3), 59-65).

In this context, metal nanoparticles have been used as building blocks in the manufacture of biosensors, due to their ability to absorb radiation in a particular frequency spectrum and the resonance frequency of their surface plasmons.

Conductive polymers and carbon nanotubes (CNT), among other carbon-based nanomaterials, are also widely used in the construction of biosensors due to their dimensional and chemical compatibility with biomolecules (G. A. Rivas, et al, 2007).

The properties of the nanoparticles vary according to their size and composition, which facilitates various applications. The production of nanoparticles can be achieved through the application of chemical, physical or biological methods. Among them, considerable attention has been given to the biological methods for the synthesis of metallic Nanoparticles, due to the great variety of resources available in nature (Kalishwaralal K, et al; Thakkar N K, et al, 2010).

Glucose, as the main source of energy in cellular metabolism, plays an important role in the natural growth of cells. Its lack or excess can produce a harmful influence on various functions. Sucrose and starch are glucose products used naturally for the transport and storage of energy, respectively.

In the state of the art, are reported several methods for the measurement of concentration of glucose in solution, such as the detection of surface plasmons (SPR) by spectroscopy, the detection of fluorescence signals, and the transduction of electrochemical signals, between others. (Tang et al 2008).

Tang et al 2008, describe a nanobiosensor to determine serum glucose based on a mixed system of quantum dots (QDs) conjugated with concanavalin A (ConA) and with gold nanoparticles (AuNPs) functionalized with thiolized b-cyclodextrin. The sensing mechanism is based on the fluorescence resonant energy transfer (FRET) between the quantum points of CdTe (cadmium telluride) as donors to the AuNPs as energy receptors. In the presence of glucose, the AuNPs are displaced by the glucose that competes for the binding sites of the ConA, resulting in recovery of fluorescence normally attenuated by the quantum points. The increase in fluorescence intensity is proportional to the concentration of glucose in a range between 0.10-50 mm. (A New Nanobiosensor for Glucose with High Sensitivity and Selectivity in Serum Based on Fluorescence Resonance Energy Transfer (FRET) between CdTe Quantum Dots and Au Nanoparticles Bo Tang,* Lihua Cao, Kehua Xu, Linhai Zhuo, Jiechao Ge, Qingling Li, and Lijuan Yu[a] Chem. Eur. J. 2008, 14, 3637-3644).

Regarding measurement of sucrose, Bagal-Kestwal et al, present a system of gold nanoparticles mediated by invertase on an onion membrane, and its application to the sensing of sucrose. Using visible ultraviolet spectrometry, they demonstrated the characteristic peak of nanoparticles decorated by invertase in an onion membrane of around 301 nm. Upon being excited at 320 nm in the presence of sucrose, the membrane exhibits a peak of photoemission at 348 nm. The lifetime of the fluorescence of the membrane modified with gold nanoparticles was 6.20 ns, compared to 2.47 ns for the membrane mediated by invertase without gold nanoparticles. (Invertase-nanogold clusters decorated plant membranes for fluorescence based sucrose sensor Dipali Bagal Kestwal, Rakesh Mohan Kestwal and Been-Huang Chiang Bagal-Kestwal et al., Journal of Nanobiotechnology (2015) 13:30 DOI 10.1186/SI2951-015-0089-1).

In the field of patents, the application US20130065777 is observed in the state of the art close to the invention, which describes a biosensor of plasmonic nanostructure comprising a substrate and a metallic film disposed on the substrate, wherein said film metal comprises one or more surfaces comprising a plurality of nanoelements arranged in a predefined pattern.

The substrate comprises silicon, silicon dioxide, silicon nitride, diamond, quartz, magnesium fluoride (MgF$_2$), calcium fluoride (CaF2), ZnSe, germanium, or a polymer. The biosensor object of analysis employs a noble metal, a transition metal, or an alkali metal.

The application WO2016018798 discloses a nanoparticle comprising elemental metals and metal salts, said salts being selected from the group oxides, sulphides, selenides and tellurides. Said nanoparticle is a nanoparticle comprising a metal or metal alloy core and a metal shell, the core is selected from the group consisting of Au, Ag, Cu, Co, Fe, and Pt; the shell is selected from the group consisting of Au, Ag, Cu, Co, Fe, Pt, metal oxides thereof, and combinations thereof; the bark is selected from the group consisting of Fe/Au, Fe/Fe304, and Au/Fe203. The quantum point composed of CdSe/ZnC—Cadmium Selenium (CdSe)/Zinc Sulfide (ZnS).

The application US2009020048 teaches a sensor comprising one or more quantum dots capable of generating a fluorescent resonance energy transfer (FRET) that can be attenuated by donating energy to one or more metallic nanoparticles. The metal nanoparticle is selected from one or more groups of Au, Ag, Pt. The sensor in which the specific heavy metal is one or more of $Hg^{2+}$, $Cu^{2+}$, and $Pb^{2+}$, the cover is a CdSe/ZnS core-shell.

The application KR20110122320 discloses a method for detecting nucleic acid comprising: A step of preparing quantum points; a step of connecting a probe containing oligonucleotides of complementary sequences for a nucleic acid on the surface of the quantum dot to form a bioconjugate quantum probe-point; the method further comprises a step of fluorescence signal detection by FRET. The quantum point has a CdSe/ZnS structure. The surface of the quantum dot is encapsulated or modified with the hydroxy group (—OH), a carboxyl group (—COOH), amino group (—NS2), or thiol group (—SH).

The application DE102014203254 discloses the architecture of a nanoparticle where the donor and the acceptor is a luminophore. The quantum point can be of the CdSe type (cadmium selenium) and has an organic coating (fluorophore).

OBJECT OF THE INVENTION

In a first object, the present invention relates to the functionalization process of synthesized gold nanoparticles functionalized with polymeric ligands for the selective measurement of sucrose or starch in intracellular fluid.

In a further object, the invention discloses a nanocomposite for measuring the concentration of sucrose or starch in intracellular fluid.

The objects described above, as well as any additional objects that may arise, will be exposed to detail and with the necessary sufficiency in the specification that is disclosed below, which will constitute the basis of the set of claims.

BRIEF DESCRIPTION OF THE FIGURES

FIG. 4: Shows the scheme of nano-material for sensing UDP-glucose and ADP-glucose (AuNPs functionalized with $SH(CH_2)_{12}COOH$ ligands) in two extreme states: a) Reference state $R_1:I_1$, reflects minimum distance between fluorescein and AuNPs resulting in maximum fluorescence attenuation by AuNPs and minimal emission;

b) $R_2:I_2$ state, with the maximum number of target analytes (UDP or ADP glucose) bound to the carboxylic acid end of the ligands for a total coverage of sensing sites, and with fluorescein introduced a posteriori, results in minimal attenuation of fluorescence by AuNPs and in a maximum emission;

c) Shows the efficiency in excited energy transfer (for the different mechanisms in the SET) versus separation between fluorescein and AuNPs. The dotted line is the theoretical efficiency of the FRET, while the solid line is that of the SET—Validated on experimental data [14]. F=fluorescein; T=udp-glucose or adp-glucose, X=F or T. The shaded area corresponds to the change in excited energy transmission efficiency of fluorescein as a product of a Δ change in the distance between the fluorophore and the surface of the AuNP.

DETAILED DESCRIPTION OF THE INVENTION

Prior to the presentation of the detailed description of the invention, the definitions of some terms are described, in order to clearly and concisely identify their scope.

The term "ligand" should be understood as a molecule linked at one end and covalently to a metal atom of the AuNP and on the other to UDP-glucose, ADP-glucose or fluorescein.

Figure 1:
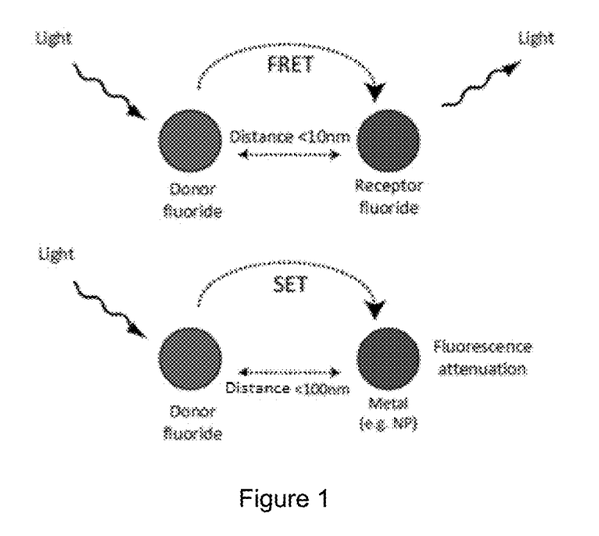
FIG. 1: Shows a scheme of the resonant fluorescent energy transfer (FRET) and surface resonance energy transfer (SET) phenomena.

The fundamental mechanism of the FRET [1] technique (Foster or Fluorescent Resonant Energy Transfer) involves a donor fluorophore molecule capable of transferring energy from excited electronic states to another receptor fluorophore molecule (the donor and receptor pair is called pair FRET), (See FIG. 1 above).

For this, the spectrum of absorption (or excitation) of the receptor molecule must overlap with the emission spectrum of the donor molecule. The transfer of energy is not given by radiative means, but by coupling of opposite charges between the two molecules (dipole-dipole interactions), in a range of approximately 10 to 100 Å. This occurs because the radio between the FRET pair is less than the wavelength of the energy released by the donor, resulting in near-field communication.

The energy transfer efficiency of the FRET is inversely proportional to the distance between the donor and the receiver raised to the sixth power, which allows to measure with high precision the distance between the FRET pair. With proper excitation, the electrons of the donor molecule jump from their base state (called S0, or minimum energy) to a higher vibrational level. In a matter of picoseconds, these electrons decay to the lowest vibrational level (called S1) and eventually (in nanoseconds) they return to their base state (S0); in doing so, they emit a photon of light. These emissions are used to determine the number of FRET interactions or to determine the distance between donor and receptor FRET molecules.

Employing a formalism similar to that of FRET Chance, Prock, and Silbey [2] describe the rate of energy transfer from a dipole to a transition between electronic bands on the surface of a metal [2-5], which then Persson and Lang [5] extend to the electrons of the metal conduction band (See FIG. 1 below). This type of transfer is called a surface energy transfer (SET).

Under these conditions, the nanomaterial object of the present invention makes use of the SET phenomenon between low molecular weight fluorophores and functionalized metal nanoparticles (NPs) to allow the selective measurement of UDP-glucose ($C_{15}H_{24}N_2O_{17}P_2$) or ADP-glucose ($C_{16}H_{25}N_5O_{15}P_2$) in solution. The presence of a fluorophore and a metallic NP with overlapping emission and reception spectra allows the use of the ratio of intensities to quantitatively detect the level or concentration of analytes present in solution.

In the preferred embodiment of the invention, the NPs used in the nano sensor compound are of gold (Au), (hereinafter AuNPs). AuNPs have unique colorimetric, conductive, and optical properties that can be syntonized based on their size, shape, and surrounding chemical environment. Therefore, although in the preferred embodiment of the invention AuNPs are related, the process is susceptible to the application of any type of ductile transition metal nanoparticles that are susceptible to absorption of fluorescence and plasmonic resonance.

On its surface, it can also be functionalized with organic ligands to bind and selectively detect different molecular targets. Finally, the distance limitation between the conventional FRET pair (<10 nm) can be reduced by coupling surface plasmons in metallic NPs [6] which allows to extend the transfer of excited electronic energy between the FRET pair at distances close to 100 nm (10 times higher than in a conventional FRET pair) and at the same time it allows to attenuate different emission frequencies, [7, 8] thanks to its high molar extinction coefficients and wide energy bandwidth, [9, 10] in the range of visible to near infrared (i.e. it acts as a receptor fluorophore).

This turns the AuNPs into ideal scaphoids for the manufacture of chemical and biological sensors, as evidenced by the increase in scientific publications associated with the detection of ions, small molecules and even cellular processes. [11]

The method for obtaining the nano-sensor compound object of the present invention consists of AuNPs between 20±5 nm in diameter as a chemically inert platform, functionalized with molecular elements for the selective detection of UDP-glucose and ADP-glucose.

The detection mechanism involves the permeation of the analytes in the solvent with AuNPs and their selective interaction with the detection components causes changes in the intensity of detectable fluorescent emission.

Figure 2:
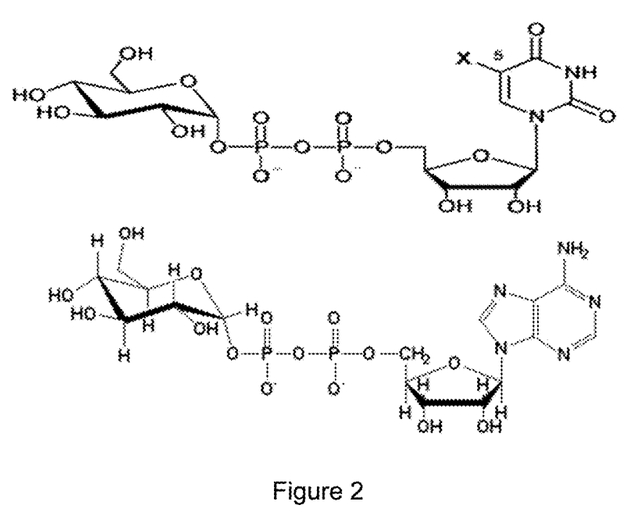
FIG. 2: Shows the scheme (left) UDP-glucose and (right) ADPglucose.

UDP-glucose and ADP-glucose (see FIG. 2) play an important role as intermediates in the metabolism of sucrose and starch, respectively.

At the biological level, there is a set of biochemical reactions both of synthesis and degradation of biomolecules that allow the maintenance and regulation of the structure and cellular function.

In plants, sucrose production and starch synthesis are two main mechanisms for transport and carbon stock, respectively. Sucrose is the main transport form of photo assimilated carbon (from the consumption of carbon dioxide during the process of photosynthesis), as well as a source of skeletal carbon and energy for the organs that do not perform photosynthesis. On the other hand, plants form starch as a polymer, from the product of photosynthesis (glucose), and use it to store energy; indispensable for its growth.

Sucrose is produced in the cytosol and starch in cellular chloroplasts. Its synthesis processes share similar mechanisms, except that in the sucrose biosynthesis the UDP-glucose is given as metabolic intermediate and in the case of starch biosynthesis it is the ADP-glucose. [12, 13]

Method for the detection of UDP-glucose and ADP-glucose (selectivity and sensitivity).

Figure 3:
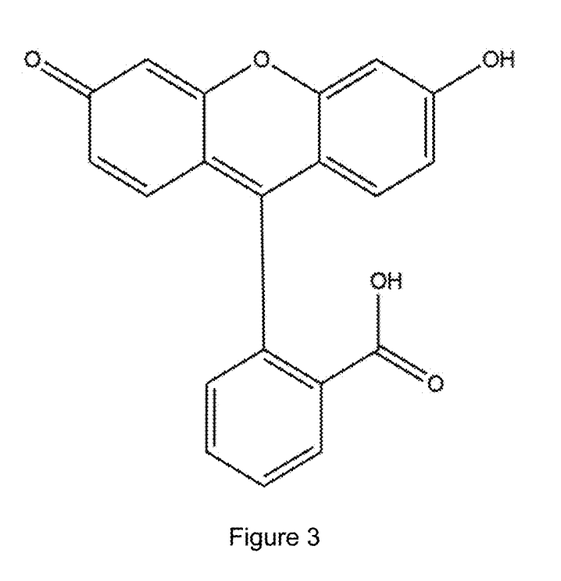
FIG. 3: Fluorophore Fluorescein.

In its preferred embodiment, the invention employs the SET phenomenon between fluorescein (FIG. 3) as fluorophore donor of energized electronic energy, and AuNPs, as attenuators/quenchers of fluorescein fluorescence, to indirectly determine the concentration of sucrose/starch in solution. The measurement mechanism is described graphically in FIG. 4.

Using the Fermi Gold Rule, the energy transfer rate of a FRET pair ($k_{EnT}$) to the product, is related between the interacting elements of the donor (FD) and the receiver (FR), $k_{EnT} \approx F_D F_R$. These elements of interaction can be simplified in such a way that the dependencies of distance between them (d) are geometric function of their arrangement in space.

For simple dipoles, $F \approx 1/d^3$, for dipole arrays in 2D, $F \approx 1/d$, and for dipole arrays in 3D, F=constant such that the power of the distance factor decreases as the dimension grows. [5] Conventional FRET consists of two simple dipoles, such that $k_{FRET} \approx F_D F_R \approx (1/d^3)(1/d^3) \approx 1/d^6$. In fact, the FRET efficiency rate is commonly written as:

$$k_{FRET} = \frac{1}{\tau_D}\left(\frac{R_0}{R}\right)^6$$

The Forster radius ($R_0$) is a function of the oscillator strength of the donor molecule and the receptor molecule, their mutual resonant energy, and the dipole addition vector. Typically, d<100 Å.

The transfer rate for the SET is estimated as $k_{SET} \approx F_D F_R \approx (1/d^3)(1/d) \approx 1/d^4$. The dipole-surface transfer energy form is then:

$$k_{SET} = \frac{1}{\tau}\left(\frac{d_0}{dt}\right)^4$$

Wherein the characteristic distance dimension is given by:

$$d_0 = \left(0.525 \frac{c^3 \phi_D}{\omega^2 \omega_f k_f}\right)$$

and it is a function of the quantum efficiency of the donor ($\phi_D$), the frequency of the electronic transition in the donor ($\omega$), the frequency of Fermi ($\omega_f$) and the Fermi wave vector ($k_f$) of the metal.[2] As a consequence, the interaction of the fluorophore with the metal surface changes depending on the distance regime. At short distances (<10 Å), the radiative coupling rate dominates; [15] at intermediate distances (20-300 Å), the transfer energy dominates; [5] and at long distances (>500 Å), fluorescent oscillations of the mirror-dipole take precedence. [2]

In a general way, quantum efficiency in energy transfer can be written as, $$\phi_{ET} = \frac{1}{1+\left(\frac{r}{r_0}\right)^n}$$

Where, for the case of dipole-dipole energy transfer, n=6 and $r_0 = R_0$, while for the case of dipole-surface energy transfer, as presented here, n=4 and $r_0 = d_0$. This allows identification of the nature of the energy transfer mechanism by questioning the slope of the efficiency curve in energy transfer versus separation distance between the donor and the receiver.

Figure 4:
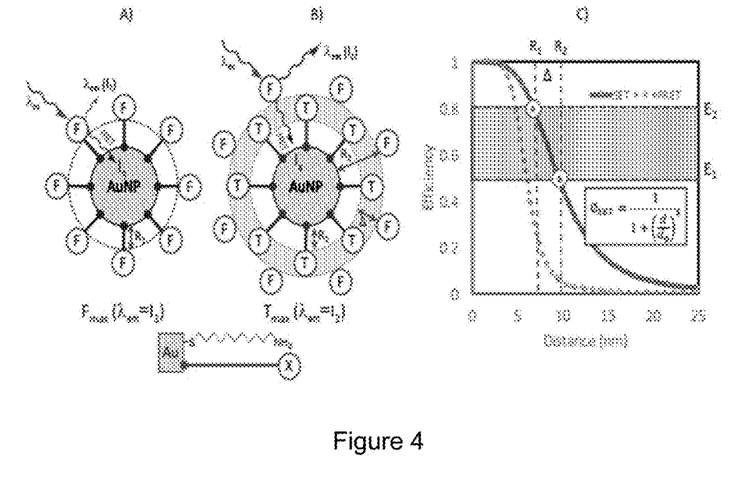

The mechanism for detecting and measuring the concentration of the analyte in solution is then derived from relating the distance between fluorescein and AuNP with the efficiency of fluorescence emission, as shown in FIG. 4 c). As an example, let's suppose we have an AuNP in solvent, with 8 active sites and 4 molecules of UDP-glucose linked to the carboxylic functional groups of AuNP (FIG. 5A).

Figure 5:
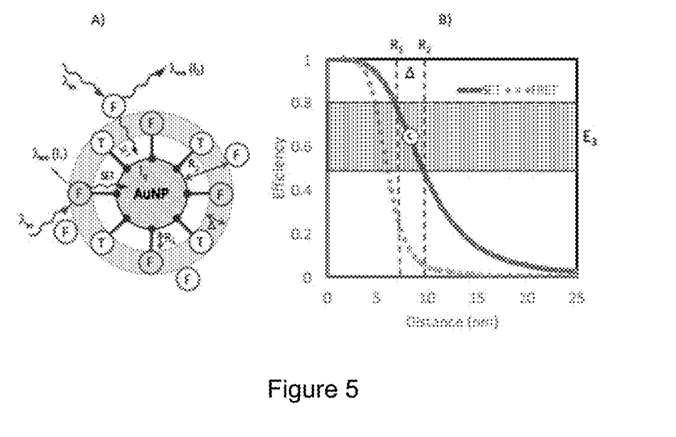
FIG. 5: Shows the SET efficiency obtained in the process of 65% for 4 UDP/ADP-glucose on the surface of the functionalized AuNP.

By introducing 8 fluoresceins in the solvent with the AuNP and the 4 UDP-glucose molecules, the SET attenuation of each fluorescence is reduced to E(R2)=0.5 for each UDP-glucose coupled to the AuNP, for a net attenuation of (4*0.5+4*0.8)/8=0.65, equivalent to 65% (FIG. 5 b).

If the 8 carboxyl sites were each linked to a fluorescein, the fluorescence attenuation for the AuNPs system would be the maximum by the SET transfer, i.e. (8*0.8)/8=0.8, which would equal 80% (FIG. 4 C).

Each UDP-glucose molecule coupled to the AuNP by the carboxylic ligand reduces the SET efficiency by 3.75%, in other words, increases the net fluorescence of the system in the same proportion (i.e. assuming, as in this case, that the number of molecules to be sensed and the number of fluoresceins is the same).

If we consider that this separation distance should include the physical size of a UDP/ADP-glucose molecule and steric repulsions at finite temperature (300K), A could exceed 2 nm (a larger Δ, further increases the net fluorescence of the system).

The percentage effect is reduced in proportion to the total number of functional active sites available in solution, assuming the same number or more of fluoresceins. That is, if the number of active functional sites increases to 16, the total intensity is now distributed among 16 photons (instead of the 8 in the previous example) and the contribution per site will be 1.875%, and so on. Partial coverage states are measured with a resolution within the range of efficiency established by the two extreme states, points A and B in FIG. 4C.

The efficiency of the energy transfer (E), $E=1-I_D/I_\infty$, is monitored by means of continuous wave photoluminescence spectroscopy (cw-PL) of the amount of fluorescein.

In one of its objects, the present invention discloses a method of functionalizing gold nanoparticles synthesized with citric acid in solution to ensure its dispersion, and functionalized with polymeric ligands for the selective measurement of sucrose or starch in cells.

In its preferred embodiment, the method comprises the following steps:

a) Synthesizing gold nanoparticles in solution with citric acid;
b) Functionalizing the synthesized gold nanoparticles (a) with the polymeric ligands $SH(CH_2)_{12}COOH$; the ligands displace the citrate groups in solution and guarantee dispersion of the AuNPs by steric repulsion.
c) Adding half a portion of the functionalized AuNPs nanoparticle solution obtained in step b) to a cytosol solution; stir.
d) Resting until achieving thermal equilibrium of the solution obtained in c), that is, until all UDP- or ADP-glucose molecules are bound in active carboxylic terminals of the AuNPs;
e) Adding fluorescein gradually to the remaining half portion of solution of functionalized AuNPs obtained in c). Stir and equilibrate until minimizing the resulting fluorescent emission—corresponds to occupy all the reactive carboxylic sites available in the solution of AuNPs functionalized with fluoresceins and results in the concentration of fluorescein required for maximum attenuation of the fluorescence by the AuNPs.
f) Adding the same concentration of fluorescein obtained in step e) to the half portion of solution of AuNPs functionalized in cytosol, obtained in step d).—corresponds to occupying the remaining active sites in solution c) with fluorescein (partial attenuation of fluorescence) and an excess of unbound fluorescein (fluorescence not attenuated);
g) Calculating the difference of the fluorescence intensity measurement between the solution of AuNPs functionalized in e) and the fluorescein solution in f). The concentration of UDP- or ADP-glucose (sucrose or starch, respectively) will be proportional to said differential calculus in the fluorescent intensity.

The examples described below are presented with the aim of describing the preferred aspects of the invention but do not constitute a limitation to the scope thereof.

Example 1

For a defined volume (vi) of solvent with an average pH of 7.2 (in the range for cytosol of 7.0-7.4 and 8.0 for the chloroplast stroma) and without electrophilic attack sensitive groups:

a) A defined concentration ($c_1$) of fluorescein is introduced and the intensity ($I_1$) of its emissions (a ~521 nm) is recorded before radiative excitation at a wavelength of 494 nm.
This would be the control sample.
b) In another sample of the same solvent and with the same volume $v_1$, a specific concentration of AuNPs functionalized with the ligand ($c_2$, estimated as described below) is introduced and gradually mix fluorescein up to a maximum concentration of $c_1$, exciting the system at 494 nm wavelength in each addition and giving time to balance the emission to the minimum (i.e. allow time for the fluorescein to be coupled to the functional active carboxylic sites of the AuNPs) intensity captured at the maximum wavelength (~521 nm). Record the concentration of fluorescein ($c_3$) before an incremental change in the intensity of the emission (12), i.e. at the time of saturation with fluoresceins of active functional carboxylic sites. It should be verified that the lifetimes of the AuNP-fluorescein conjugate system for the different concentrations are similar and dialyze (purify) the mixtures to remove unreacted fluorescein. It would correspond to the state shown in FIG. 4 a).
c) Introduce a concentration ($c_2$) of the functionalized AuNPs with the ligand in a cytosol/stroma sample; mix and let stand for 15 minutes.
d) Introduce a concentration ($c_3$) of fluorescein into the mixture, mix and let stand until maximizing the fluorescence (13) of the system.
e) Calculate the concentration of UDP/ADP-glucose as a function of the net intensity of the fluorescent emission (i.e. with respect to the control sample), as explained above.

The concentration $c_2$ would be estimated according to the number of active functional carboxylic sites, and directly proportional to the number of AuNPs/L, the size distribution of its size, the surface coverage of the ligands on the AuNPs and the functionalized surface coverage and with analytes bound by the carboxyl group that results in minimal energy.

The measurement of these nucleotide sugars by the proposed nano-sensing system allows to derive the concentration of sucrose in the cytosol (or the concentration of starch in the chloroplast) in plants at a lower limit of nano-moles ($10^{-9}$), versus the lower limit using techniques in the state of the art of micro-moles ($10^{-6}$)[16] or traditional experimental techniques such as chromatography and mass spectrometry, which provide a resolution in the measurement of carbohydrate concentration in the scale of the milli-moles ($10^{-3}$).

Example 2

Synthesis and Functionalization of AuNPs.

AuNPs are produced in a solvent by the chemical reduction of chloroauric acid ($H[AuCl_4]$), [17] although there are more precise and advanced methods to date.[18-20] After dissolving $H[AuCl_4]$, the solution it mixes rapidly in the presence of a reducing agent. This reduces the Au3+ ions to neutral gold atoms. As more and more gold atoms form, the solution becomes super-saturated, and the gold begins to gradually precipitate in the form of sub-nanometric particles. The rest of the gold atoms adhere to the existing particles, and to achieve nano-particles of uniform size the solution is vigorously stirred.

Figure 6:
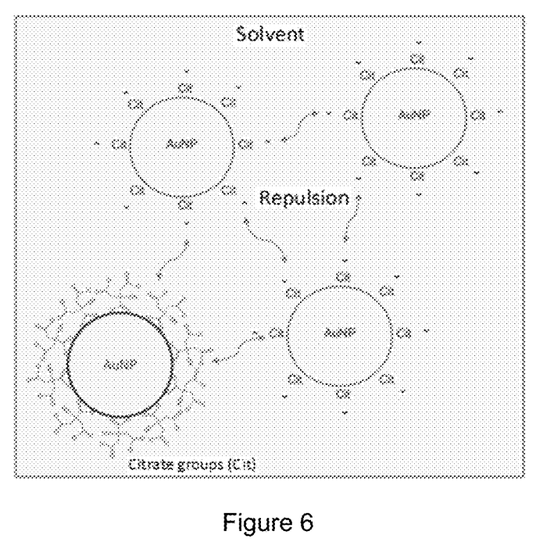
FIG. 6: Shows the dispersion of AuNPs in citrate solution.

To prevent aggregation of the AuNPs, a stabilizing agent that is physically absorbed (i.e. low energy, non-covalent interaction) is introduced to the surface of the AuNPs. In this case, we use citrate groups that introduce a net negative charge on the surface of the AuNPs (that is, a high Z potential). The electrostatic repulsion between surfaces leads to keeping the dispersed AuNPs in solution, as shown in FIG. 6.

Functionalization of the AuNPs with 12-Thiol-Dodecanoic Acid.

We exchanged the citrates for 12-thiol-dodecanoic acid, SH(CH2)12COOH. The sulphated groups displace the citrate molecules on the surface of the AuNPs as a consequence of the strong affinity between the gold surface and the sulfide. The polar carboxyl groups of the ligand guarantee hydrophilicity. The exchange avoids the aggregation of the AuNPs by steric repulsion and allows one to functionalize by self-assembly.

Chemical Absorption of UDP/ADP-Glucose on 12-Thiol-Dodecanoic Acid

The chemical reactivity of the uracil ring of UDP-glucose is explained by the presence of the two carbon atoms, C-5 and C-6, which present a differential reactivity to electrophilic and nucleophilic reagents.

In other words, the uracil ring is characterized by having a Carbon (C-5) susceptible to an electrophilic attack, because it has two carbonyl groups that activate the C-5, giving it a slightly more negative charge than would occur in the absence of such activating groups and a Carbon susceptible to undergoing a nucleophilic attack, (C-6), which is the β-carbon of an α, β-unsaturated carbonyl system. The positive or negative charges that are formed on the uracil ring during the reaction are stabilized by resonance within the ring, increasing the reactivity of said system.

The functional chain $SH(CH_2)_{12}COOH$ linked by its sulfhydryl end to the surface of an AuNP interacts with the C-5 of the uracil ring, through the carbonyl carbon of its carboxyl terminus. As previously mentioned, the C-5 of the uracil ring of the UDP-glucose, when presenting a charge slightly negative, will nucleophilically attack the C of the carbonyl group, C=O that presents a slightly positive charge of the ligand through a nucleophilic substitution reaction, eliminating a molecule of water.

Chemical Absorption of Fluorescein on 12-Thiol-Dodecanoic Acid

In the same way to the process described in the previous paragraph, the negatively charged oxygen of the dianion flurecein at pH equal to or greater than 6.4 (see FIG. 1), as well as the C in position for the carboxyl group of the benzoic ring of the fluorescein can nucleophilically attack the C=O of the ligand, competitively to UDP-glucose; this allows to form a covalent bond that integrates the AuNP-ligand-UDP-glucose complex. Similarly, the adenine ring allows the binding of the 12-thiol-dodecanoic acid ligand to the reactive functional carboxylic group.

In the absence of fluorescein the ligand will bind preferably to the C-5 of the uracil ring of the UDP-Glucose and in the absence or deficiency of UDP-Glucose the excess of ligand bound to the gold nanoparticle will be added to the C of the C=O or to the para-C of the benzoic ring of fluorescein.

The Following Sequence of Reactions Graphically Describes What was Outlined in the Two Previous Numerals:

Reaction of UDP-Glucose with the Ligand Bound to the NPAu

Dianion Fluorescein Reaction, by the Carbon in Position Para of the Benzoic Ring with the Ligand Bound to the AuNP Dianion Fluorescein Reaction, by the Phenolate End with the Ligand Bound to the AuNP Fluoresceins functionalized with the polymeric extension (c) have a covalent affinity for the residual group (R) with the nucleotide sugars of the UDP-glucose and ADP-glucose type.

The physical adsorption of fluorescein on the surface of an AuNP results in the SET effect of AuNP decreasing fluorescein photoluminescence (quenching or attenuation).

Under these conditions, the composition of the Nanocomposite (nanosensor) object of the present invention incorporates Fluorescein in solution and gold Nanoparticles synthesized with citric acid in solution functionalized with the polymeric ligands $SH(CH_2)_{12}COOH$, where the ligand $SH(CH_2)_{12}COOH$ has a length between 2 to 5 nm.

The use of the Nanocomposite (nanosensor) object of the present invention is embodied in processes involving the measurement of sucrose or starch in cells.

Although the present invention has been described with the preferred embodiments shown, it is understood that modifications and variations that preserve the spirit and scope of this invention are understood within the scope of the appended claims.

REFERENCES

1. Jares-Erijman, E. A. and T. M. Jovin, *FRET imaging.* Nature Biotechnology, 2003. 21(11): p. 1387-1395.
2. Chance, R. R., A. Prock, and R. Silbey, *Molecular fluorescence and energy transfer near interfaces.* Adv. Chem. Phys., 1978. 37(1): p. 65.
3. Alivisatos, A. P., D. H. Waldeck, and C. B. Harris, *Nonclassical Behavior of Energy-Transfer from Molecules to Metal-Surfaces—Biacetyl(Normal-3-PiStar)/Ag (111).* Journal of Chemical Physics, 1985. 82(1): p. 541-547.
4. Kuhnke, K., R. Becker, M. Epple, and R. Kern, *C-60 exciton quenching near metal surfaces.* Physical Review Letters, 1997. 79(17): p. 3246-3249.
5. Persson, B. N. J. and N. D. Lang, *Electron-Hole-Pair Quenching of Excited States near a Metal.* Physical Review B, 1982. 26(10): p. 5409-5415.
6. Ray, P. C., G. K. Darbha, A. Ray, J. Walker, and W. Hardy, *Gold nanoparticle based FRET for DNA detection.* Plasmonics, 2007. 2(4): p. 173-183.
7. Ghosh, D. and N. Chattopadhyay, *Gold and silver nanoparticles based superquenching of fluorescence: A review.* Journal of Luminescence, 2015. 160: p. 223-232.
8. Chen, C. X., D. Zhao, J. Sun, and X. R. Yang, *A dual-mode signaling response of a AuNP-fluorescein based probe for specific detection of thiourea.* Analyst, 2016. 141(8): p. 2581-2587.
9. Sapsford, K. E., L. Berti, and I. L. Medintz, *Materials for fluorescence resonance energy transfer analysis: Beyond traditional donor-acceptor combinations.* Angewandte Chemie-International Edition, 2006. 45(28): p. 4562-4588.
10. Jain, P. K., I. H. El-Sayed, and M. A. El-Sayed, *Au nanoparticles target cancer.* Nano Today, 2007. 2(1): p. 18-29.
11. Lee, Y. E. K., R. Smith, and R. Kopelman, *Nanoparticle PEBBLE Sensors in Live Cells and In Vivo.* Annual Review of Analytical Chemistry, 2009. 2: p. 57-76.
12. Wang, Q. H., X. Zhang, F. G. Li, Y. X. Hou, X. L. Liu, and X. Y. Zhang, *Identification of a UDP-glucose pyrophosphorylase from cotton (Gossypium hirsutum L.) involved in cellulose biosynthesis in Arabidopsis thaliana.* Plant Cell Reports, 2011. 30(7): p. 1303-1312.
13. Tiessen, A. and D. Padilla-Chacon, *Subcellular compartmentation of sugar signaling: links among carbon cellular status, route of sucrolysis, sinksource allocation, and metabolic partitioning.* Frontiers in Plant Science, 2013. 3.
14. Yun, C. S., A. Javier, T. Jennings, M. Fisher, S. Hira, S. Peterson, B. Hopkins, N. O. Reich, and G. F. Strouse, *Nanometal surface energy transfer in optical rulers, breaking the FRET barrier.* Journal of the American Chemical Society, 2005. 127(9): p. 3115-3119.
15. Dulkeith, E., A. C. Morteani, T. Niedereichholz, T. A. Klar, J. Feldmann, S. A. Levi, F. C. J. M. van Veggel, D. N. Reinhoudt, M. Moller, and D. I. Gittins, *Fluorescence quenching of dye molecules near gold nanoparticles: Radiative and nonradiative effects.* Physical Review Letters, 2002. 89(20).
16. Bagal-Kestwal, D., R. M. Kestwal, and B. H. Chiang, *Invertase-nanogold clusters decorated plant membranes for fluorescence-based sucrose sensor.* Journal of Nanobiotechnology, 2015. 13
17. Turkevich, J., P. C. Stevenson, and J. Hillier, *A Study of the Nucleation and Growth Processes in the Synthesis of Colloidal Gold.* Discussions of the Faraday Society, 1951 (11): p. 55-&.
18. Brust, M., M. Walker, D. Bethell, D. Schiffrin, and R. Whyman, *Synthesis of 5 Thiol-derivatised Gold Nanoparticles in a Two-phase Liquid-Liquid System.* J. Chem. Soc., 1994(7): p. 801-802.
19. Perrault, S. D. and W. C. W. Chan, *Synthesis and Surface Modification of Highly Monodispersed, Spherical Gold Nanoparticles of 50-200 nm.* Journal of the American Chemical Society, 2009. 131(47): p. 17042-+.
20. Martin, M. N., J. I. Basham, P. Chando, and S. K. Eah, *Charged Gold Nanoparticles in Non-Polar Solvents: 10-min Synthesis and 2D Self Assembly.* Langmuir, 2010. 26(10): p. 7410-7417.
21. Elfeky, S. A. and A. A. Al-Sherbini, *Synthesis and Spectral Characteristics of Gold Nanoparticles Labelled with Fluorescein Sodium.* Current Nanoscience, 2011. 7(6): p. 1028-1033.

The invention claimed is:
1. Method for the measurement of sucrose or starch in in plant cells which comprises the steps of:
   a) Synthesizing gold nanoparticles (AuNPs) in solution with citric acid;
   b) Functionalizing the synthesized gold nanoparticles obtained in step a) with the polymeric ligands SH(CH2)12COOH to provide a polymer functionalized AuNPs and dispersing a defined concentration of the polymer functionalized AuNPs to provide a polymer functionalized AuNPs solution;

c) Adding half a portion of the polymer functionalized AuNPs solution obtained in step b) to a cytosol solution or a chloroplast solution obtained from the plant cells;
d) Resting until achieving thermal equilibrium of the solution obtained in c);
e) Adding a defined concentration of fluorescein to the remaining half portion of the polymer functionalized AuNPs solution of step b);
f) Adding the same defined concentration of fluorescein used in step e), to the thermal equilibrated solution obtained in step d) having the polymer functionalized AuNPs solution and the cytosol or chloroplast solution;
g) Measuring fluorescence intensity of the solution obtained in step e) and step f) and obtaining a net intensity of fluorescence from the difference of the measured fluorescence intensity of the solution between step e) and step f); and
h) measuring the concentration of UDP-glucose or ADP-glucose as a function of the measured net intensity obtained in step g), and determining the concentration of sucrose or starch in the cytosol solution or the chloroplast solution from the measured concentration of the UDP-glucose or the ADP-glucose.

2. The method for the measurement of starch in the plant cells according to claim 1, wherein in step c), the polymer functionalized AuNPs solution obtained in step b) are added to the cellular chloroplast solution obtained from the plant cells.

3. The method for the measurement of sucrose or starch in cells according to claim 1, wherein the AuNPs have a diameter between 20±5 nm.

4. The method for the measurement of sucrose in the plant cells according to claim 1, wherein in step c), the polymer functionalized AuNPs solution obtained in step b) are added to the cellular cytoplasm solution obtained from the plant cells.

* * * * *